United States Patent [19]
Onodera

[11] Patent Number: 6,012,576
[45] Date of Patent: *Jan. 11, 2000

[54] METHOD OF STORING BRUSH USED IN SUBSTRATE SURFACE TREATMENT AND CONTAINER FOR STORING SUCH BRUSH

[75] Inventor: Naoko Onodera, Kawasaki, Japan

[73] Assignee: Fujitsu Limited, Kawasaki, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/684,859

[22] Filed: Jul. 25, 1996

[30] Foreign Application Priority Data

Jul. 26, 1995 [JP] Japan ................................. 7-190455

[51] Int. Cl.⁷ ................................................. B65D 83/10
[52] U.S. Cl. .......................... 206/361; 206/446; 206/209; 15/184
[58] Field of Search ................................... 206/361, 722, 206/723, 446, 209, 397, 407, 408, 207; 15/184, 257.01, 257.05, 258; 132/313, 317

[56] References Cited

U.S. PATENT DOCUMENTS

| | | | |
|---|---|---|---|
| 1,459,831 | 6/1923 | Jones | 206/209.1 |
| 2,654,504 | 10/1953 | Hyams | 206/209 |
| 2,782,909 | 2/1957 | McNamara | 206/209 |
| 2,945,251 | 7/1960 | Eichner | 206/209 |
| 3,393,412 | 7/1968 | Wrbican | 206/209 |
| 3,918,582 | 11/1975 | Wallace | 206/209 |
| 4,151,914 | 5/1979 | Blatt | 206/408 |
| 4,473,152 | 9/1984 | Jump, Jr. et al. | 206/209 |
| 4,771,501 | 9/1988 | Leiter | 15/104.92 |
| 4,865,188 | 9/1989 | Custeau | 206/209 |
| 5,086,916 | 2/1992 | Gray | 206/209 |
| 5,511,654 | 4/1996 | De La Rocha | 206/361 |
| 5,709,301 | 1/1998 | Couch et al. | 206/361 |

FOREIGN PATENT DOCUMENTS 24400  12/1993  United Kingdom ................... 206/408

*Primary Examiner*—Paul T. Sewell
*Assistant Examiner*—Nhan T. Lam
*Attorney, Agent, or Firm*—Armstrong, Westerman, Hattori, McLeland & Naughton

[57] ABSTRACT

A brush used for scrubbing is stored in a container, when not being used, in a wet state. The brush to be stored may be dipped in a bactericidal liquid which may be filled in a container with a removable top. The container is constructed such that the sponge or fibrous member of the brush is supported, so as not to experience any deforming stress. Before storage, the brush and the container may be subjected to bactericidal heating. Materials of the container and top are selected taking into account the chemical stability of the materials with respect to the liquid used, and the heat resistance of the material with respect to bactericidal heating.

11 Claims, 3 Drawing Sheets

METHOD OF STORING BRUSH USED IN SUBSTRATE SURFACE TREATMENT AND CONTAINER FOR STORING SUCH BRUSH

BACKGROUND OF THE INVENTION

1. Field of the Invention

The present invention relates to a method for storing a brush used in a scrubbing process, and a container for storing such brush. The scrubbing process is performed, during the manufacturing process of an electronic device, to wash, make smooth, or impart a particular property to the surface of the semiconductor wafer or other substrate like a glass plate, on which the electronic device with a precise pattern is formed.

2. Description of the Related Art

In the manufacturing of a semiconductor device a dielectric film made of $SiO_2$ or $Si_3N_4$, or a conductive film made of, for example, TiN or polysilicon, is deposited on the surface of, for example, a semiconductor wafer. A chemical vapor deposition device or a sputtering device is used for the film deposition. When a film is being deposited by either of these devices, however, a film is also deposited onto an inner wall or an inner mechanism of a reaction chamber of the chemical vapor deposition device or of a vacuum chamber of the sputtering device. As the film gets thicker, it peels off as fine particles into the space in the reaction chamber or the vacuum chamber, and either sticks onto the surface of the desired thin film on the wafer, or is embedded into the thin film growing on the wafer, whereby a protrusion is formed, thus deteriorating the characteristics of a semiconductor device formed on the wafer and making the semiconductor device less reliable. Accordingly, the fine particles on the surface of a wafer or substrate are scrubbed away by a brush. In the manufacturing of a liquid crystal display (LCD) panel, the inner surface of a glass substrate is scrubbed using a brush in order to impart a property for aligning the orientation of the liquid crystal molecules to the surface.

The brush used for scrubbing the surface of a wafer or substrate formed of a fibrous or sponge-like member is attached to the surface of a disk-shaped member or a cylindrical surface of a drum-shaped member. The fibrous or sponge-like member is made of, for example, synthetic high polymers, such as polyvinyl alcohol, nylon, rayon, or polypropylene. The material is selected depending on the scrubbing to be performed, taking into account the hardness, flexibility, chemical resistance, and water resistance required. The present inventor has disclosed various brush structures (see for example Japanese Patent Application No. 05-220341).

In general, brushes formed by high polymer materials such as those mentioned above are washed after use, dried, and stored until they are used again. However, when brushes formed, in particular, of polyvinyl alcohol or rayon, and kept dry, are left exposed in the air, for example, for a few months, they change their physical and chemical nature. In other words, even when these types of brushes are made wet again, they often do not return back to their original form, recover their original resiliency, etc. Therefore, in the scrubbing process, the surface of the brush contacting to the semiconductor wafer becomes uniform, resulting in a non-uniform contact pressure therewith, so that the brush is no longer capable of scrubbing the wafer properly. In addition, brushes that have undergone physical or chemical changes cause wearing off when contacting to the wafer surface, thus making it easier for fine particles to be produced. In the scrubbing process, the fine particles stick onto the semiconductor wafer surface, so that these particles become a source of contamination.

Further, recent pattern dimensions in semiconductor integrated circuits, in terms of the gate length of a transistor for example, are in the order of a tenth of a micrometer, which is approximately equal to or less than the size of microorganisms such as bacteria. Therefore, exposing brushes, kept in a wet state, to the atmosphere causes microorganisms to multiply in the brushes. Consequently, such microorganisms are now being considered as contaminants of semiconductor wafer surfaces.

SUMMARY OF THE INVENTION

Accordingly, an object of the present invention is to provide a method for storing a brush, that is not being used, such that its physical or chemical nature is not altered, and a container or storing such a brush that is not being use.

Another object of the present invention is to provide a method for storing a brush, that is not being used, such that no microorganisms are produced or multiply in the brush, and a container for storing such a brush that is not being used.

DESCRIPTION OF THE PREFERRED EMBODIMENTS

Figure 1:
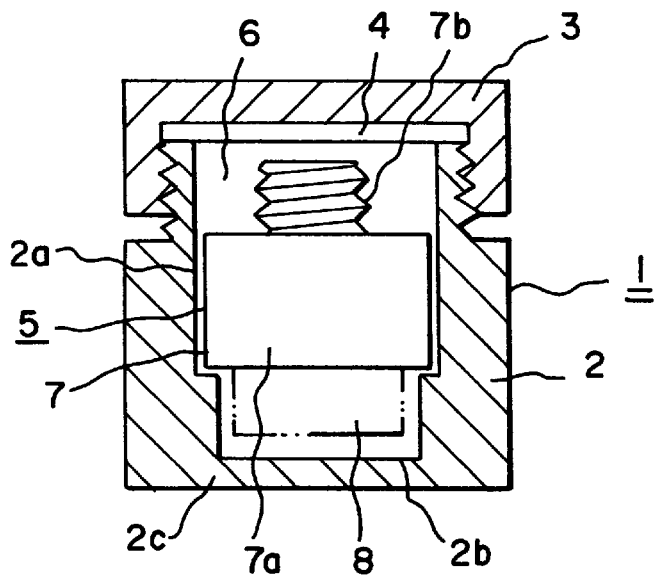
FIG. 1 is a cross sectional view of a container and a brush stored therein in an embodiment of the present invention.

Referring to FIG. 1, container 1 comprises a shell 2 and a top 3. The shell 2 has a bottom 2c, and the opening thereof at the upper end is closed by the top 3. The shell 2 and the top 3, both of which are threaded, engage each other, thereby allowing the top 3 to be fitted onto or moved away from the shell 2. A flat or annular gasket 4 is provided in order to tightly seal the shell 2 with the top 3.

A brush 5 is stored in the container 1, and as illustrated in FIGS. 3A to 3D it comprises a fibrous or sponge-like members 8 and a holder 7. The member 8 is attached to a flat surface of the holder 7. The dimensions of the shell 2 and the top 3 are determined as follows.

The side walls of the holder 7 are separated by a very small clearance of, for example, 0.5 mm from an inner wall 2a of the container, and its lower end is supported by a stepped section of the inner wall of the shell. Such a construction allows a clearance of the proper size, such as 3 mm, to be formed between the member 8 and both of the side surface and the bottom 2c of the shell 2, so that they do not contact each other. Therefore, the member 8 is supported, so as not to experience any deforming stress. Referring to FIG. 1, reference numeral 7b denotes means for securing the brush 5 to a scrubber apparatus (not shown), such as a screw. While the shell 2 is tightly sealed with the top 3, it is preferable that there be a slight clearance of, for example, 0.5 mm between the upper end of the screw 7b and the top 3.

For example, the brush 5 can be stored in the shell 2 without becoming dry by putting the brush 5, whose member 8 is soaked with water, into the shell 2 and, tightly sealing the shell 2 with the top 3. In this case, the shell 2 may be filled with water 6. In addition, when the shell 2 is filled with a bactericidal liquid or a liquid that prevents multiplication of bacteria, instead of water, it is possible to prevent bacterial contamination when the brush is to be stored for a very long time, such as a few months or about half a year. Examples of bactericidal liquids include an aqueous solution of 1 to 5% hydrogen peroxide, an aqueous solution of sodium hypochlorite or formalin, or water with ethyl alcohol or isopropyl alcohol added thereto. Another effective way to prevent bacterial contamination is to heat the top 3 along with shell 2 containing therein the brush 5 in order to kill off any bacteria, and then sealing the shell 2 with the top 3. The most preferable method to present bacterial contamination is to heat the brush 5 along with the shell 2 and the top 3 in order to kill off any bacteria, and then storing the brush 5 in a bactericidal liquid.

It is desirable that the shell 2 and the top 3 both have a heat resistance high enough to prevent them from softening and deforming at bactericidal heating temperatures of about 100° C. In addition, it is desirable that the shell 2 and the top 3 be chemically stable with respect to bactericidal liquids as those mentioned above. Common materials that meet such requirements as those mentioned above include polypropylene and ethylene tetrafluorideperfluoroalkylvinylether copolymer. Obviously, other materials may also be used, depending on the bactericidal liquid and heat treatment used. For example, other inexpensive materials such as polyethylene or polyvinyl chloride may be used, when an aqueous solution such as aqueous hydrogen peroxide solution is used.

Figure 2:
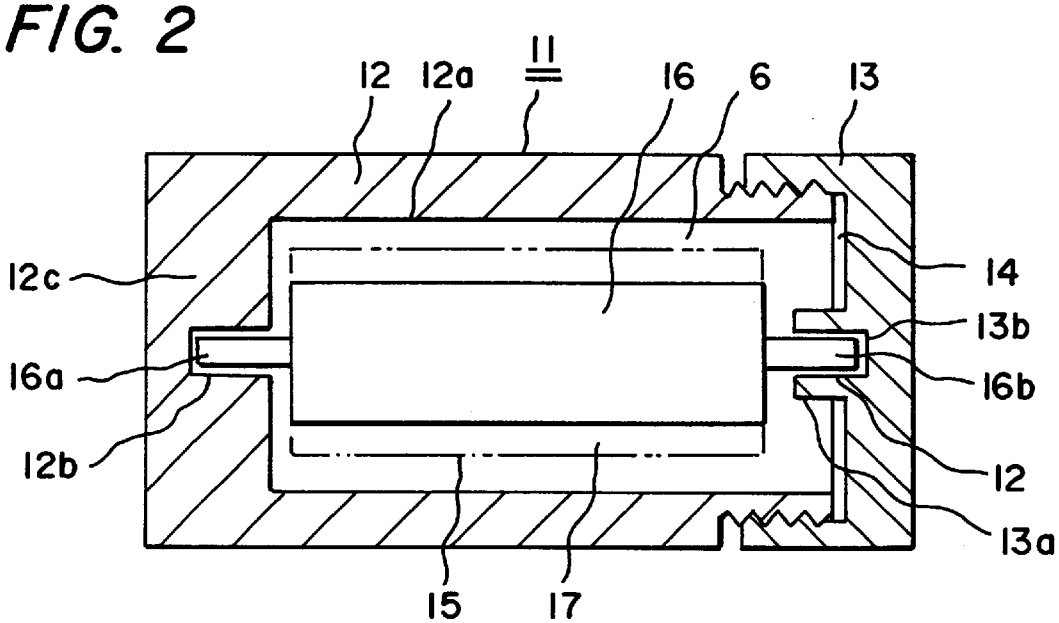
FIG. 2 is a cross sectional view of a container and a brush stored therein in another embodiment of the present invention.

FIG. 2 is a cross sectional view of a container 11 and a brush 5 stored therein in another embodiment of the present invention for storing a cylindrical brush. The container 11 comprises a shell 12 and a top 13. The shell has a bottom 12c, with its top end covered with the top 13. The shell 12 and the top 13, both of which are threaded, engage each other, thereby allowing the top 13 to be fitted onto or removed from the shell 12. A flat or annular gasket 14 is provided in order to ensure tight sealing of the shell 12 with the top 13.

Figure 4:
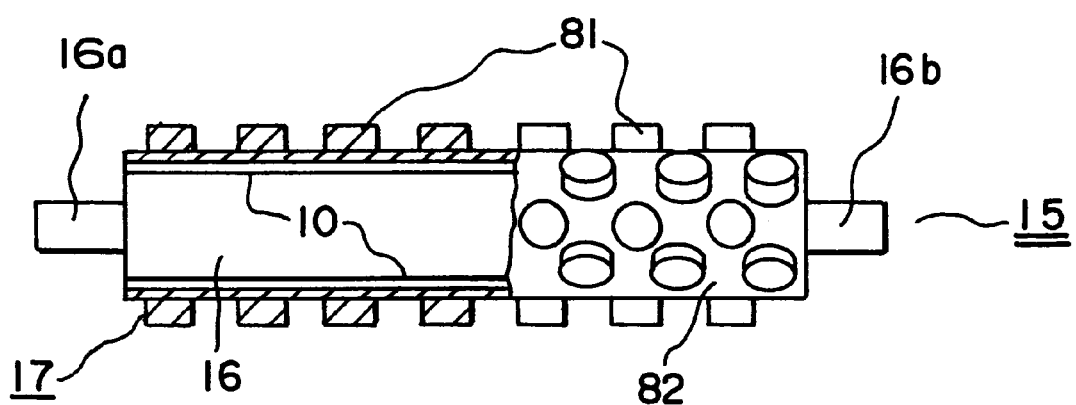
FIG. 4 is a side-elevational view of a specific structure of the container and the brush stored therein of FIG. 2.

As illustrated in FIG. 4, the brush 15, stored in the container 11, comprises a sponge-like member 17 provided with a plurality of protrusions 81, and a cylindrical holder lo. The member 17 is closely fixed to the side face of the holder 16. Shafts 16a and 16b extend along the longitudinal dimension of the holder 16 from either end of the holder 16. The shafts 16a and 16b are means for connecting the brush 15 to a scrubber apparatus (not shown). The brush 15 rotates around the shafts 16a and 16b as center.

The dimensions of the shell 12 and the top 13 are determined as follows.

Cylindrical cavities 12b and 13b that engage the shafts 16a and 16b, respectively, are formed at the bottom 12c of the shell 12 and the top 13, respectively. The brush 15, stored in the shell 12, is supported by the shafts 16a and 16b that engage the cavities 12b and 13b, respectively. With the brush 15 supported by the shafts 16a and 16b, the protrusions 81 of the member 17 fixed to the side face of the holder 16 is separated from the inner wall 12a of the shell 12 by a clearance of a proper size of, for example, 3 mm. When the top 13 tightly seals the shell 12, the clearances between the shafts 16a and 16b and the corresponding cavities 12b and 13b are both, for example, 0.3 mm in the longitudinal and radial directions. Accordingly, the brush 15 is supported in the container 11, without the protrusions 81 of the member 17 contacting the inner wall of the shell 12.

The brush 15, being wet, is stored in the shell 2, with the top 13 tightly sealing the shell 12. After heating the brush 15 along with the shell 12 and the top 13 to kill off any bacteria, it is preferable to fill the shell 12 with a bactericidal liquid 6, and store the brush 15 in the container 1 with the member 17 kept dipped in this bactericidal liquid 6. The materials for the shell 12 and the top 13 are selected based on the exact same standards as those of the container 1 of FIG. 1.

FIGS. 3A to 3D illustrate examples of the brush 5 to be stored in the container 1 in the embodiment of FIG. 1.

Figure 3A:
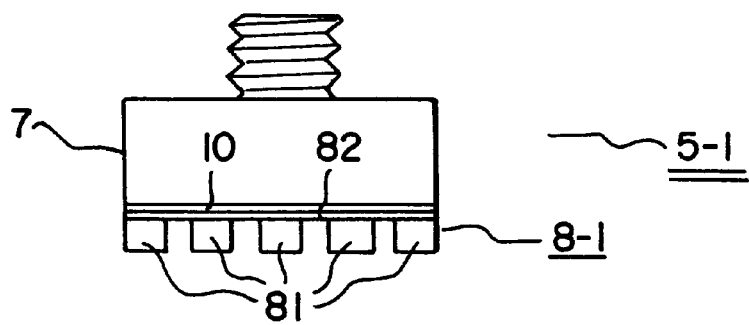
FIGS. 3A to 3D are each side-elevational views of a specific structure of the container and the brush stored therein of FIG. 1.

In brush 5-1 of FIG. 3A, a member 8-1 comprising a sheet-like base 82 provided with a plurality of protrusions 81 is affixed to a flat surface of the cylindrical holder 7 by an adhesive layer 10. The protrusions 81 and the base 82 are formed by a sponge material formed, for example, of polyvinyl alcohol (PVA).

A screw 7b is provided at the other flat surface of the holder 7 in order to allow connection of the holder 7 to a scrubber apparatus (not shown).

Figure 3B:
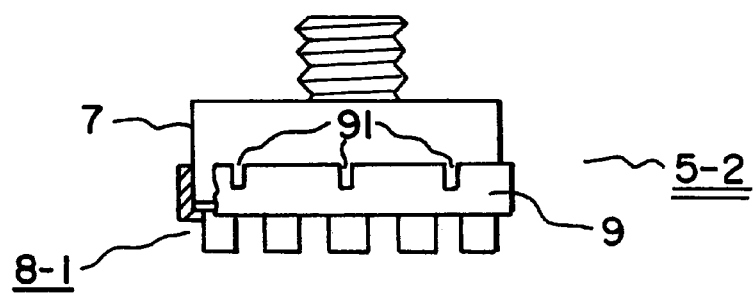

In brush 5-2 of FIG. 3B, a member 8-1 that is, for example, essentially the same as the member 8-1 of FIG. 3A is affixed to the holder 7 by an annular member 9, instead of the adhesive layer 10. The annular member 9 has a brim formed by bending. The brim, which has cut-outs 91, is resilient, making it possible to remove the brim, itself, and the member 8-1 from the holder 7.

Figure 3C:
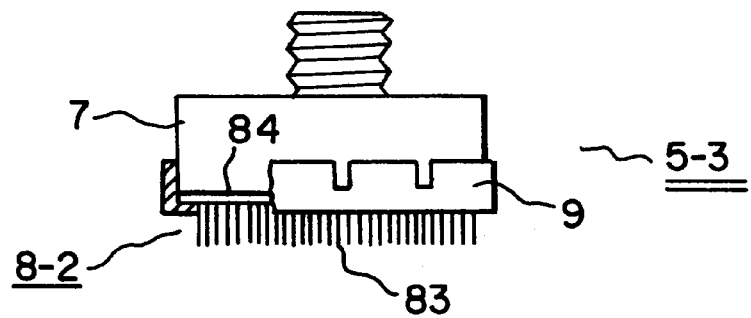

The brush 5-3 of FIG. 3C is the same as the one shown in FIG. 3B, except that a member 8-2 comprising fibrous pieces is used in place of the member 8-1 comprising sponge-like protrusions 82. The member 8-2 has a plurality of fibers 83 made of, for example rayon that are vertically attached to a base 84 that is, for example, in sheet form and made of nylon.

Figure 3D:
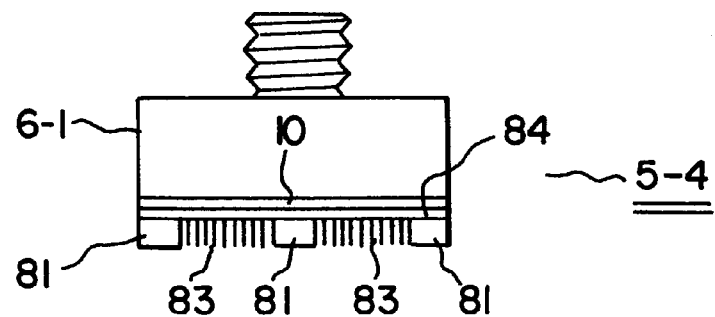

The brush 5-4 of FIG. 3D consists of a combination of sponge-like protrusions 81 illustrated in either FIG. 3A or 3B and fibers 83 shown in FIG. 3C. In the figure, parts that are essentially same as those of FIGS. 3A to 3C are given the same reference numerals.

FIG. 4 illustrates a construction of the brush 15 to be stored in the container 11 in the embodiment of FIG. 2. The member 17 comprises a base 82 provided with a plurality of protrusions 81, and is affixed to the outer surface of a cylindrical holder 16 composed of, for example, polypropylene. The protrusions 81 are made of sponge material comprising, for example, 7VA. The base 82 is composed of, for example, PVA, and is flexible. The base 82 is wrapped around the outer surface of the holder 16, and is affixed to the holder 16 by an adhesive layer 10. In the figure, reference numerals 16a and 16b denote, respectively, the rotating shafts along the axis of the holder 10.

According to the present invention, a brush formed by a sponge-like member or fibrous member is stored in a container for a few months to half a year, while it is in a wet state. The sponge-like member is supported in the container so as not to experience any deforming stress. If necessary, in order to kill off any bacteria the brush and the container storing the brush are heated, or the brush is dipped into a bactericidal liquid filled in a closed container and stored therein. Thus, the brush will not be irreversibly deformed and deteriorated, during its storage period. In addition, the brush stored in the container will not be contaminated by multiplication of bacteria. Accordingly, the present invention makes it possible to effectively maintain the scrubbing effect of the brush, after storage, and to prevent contamination of the surface of the works. Consequently, the production yield of works, such as that of semiconductors, is increased, and the life of the brush is prolonged, resulting in reduced production costs, including brush cost and maintenance cost.

The present invention method for storing a brush for scrubbing in wet condition is also effective for a brush which is attached to a scrubbing apparatus and is idle, because the brush can immediately be used when the apparatus is restarted.

What is claimed is:

1. A method for storing a brush, the brush having a portion composed of one of a fibrous and a spongy member formed from a high polymer material suitable for scrubbing a surface of a semiconductor wafer or a glass plate for a liquid crystal display, comprising removing a brush from a scrubbing apparatus and sealing the brush in a container so that the fibrous or spongy member is maintained in a wet and disinfectant condition.

2. A method for storing a brush as set forth in claim 1, wherein the brush is soaked in a liquid.

3. A method for storing a brush as set forth in claim 2, wherein the liquid has properties for at least one of killing bacteria and preventing bacteria from breeding.

4. A method for storing a brush as set forth in claim 3, wherein the liquid is a solution of a chemical selected from a group consisting of hydrogen-peroxide, hypochlorite, formaldehyde and alcohols.

5. A method for storing a brush as set forth in claim 1, wherein the brush having said one of the fibrous member and the spongy member in a wet and disinfectant condition is sealed in a container so that said one of the fibrous member and the spongy member is held without contacting the container.

6. A method for storing a brush as set forth in claim 5, wherein the brush is sealed in the container after being subjected to a steam sterilization together with the container.

7. A method as set forth in claim 1, wherein said substrate is one used in the manufacture of electronic devices wherein a surface thereof must be substantially free from contamination of particles.

8. A method for storing a brush as set forth in claim 1, wherein the high polymer material is selected from the group consisting of polyvinyl alcohol, rayon, nylon and polypropylene.

9. A method for storing a brush according to claim 1, wherein the brush is formed of a high-polymer material which cannot restore flexibility thereof when the brush is stored in a condition where the brush is dried, even if the brush is wetted again after such storing.

10. A method for preventing a brush from generating particles which contaminate a surface of a semiconductor substrate during scrubbing of the surface, the brush having a portion comprising one of a fibrous member and a spongy member which originally has a flexibility but cannot restore the flexibility and which tends to generate said particles in said scrubbing, even when the brush is wetted by a liquid after the brush has been dried, said method comprising the step of sealing said brush in a container under a wet and disinfectant condition after the brush has been used in said scrubbing.

11. A method of storing a brush which has been used to clean a semiconductor surface or a glass plate for a liquid crystal display, comprising;

removing a brush from a scrubbing apparatus after the brush has been used to clean a semiconductor surface or a glass plate for a liquid crystal display, the brush having a portion composed of one of a fibrous and a spongy member formed from a high polymer material;

sealing the brush in a container so that the fibrous or spongy member is maintained in a wet and disinfectant condition.

* * * * *